(12) United States Patent
Jordan et al.

(10) Patent No.: US 10,140,843 B2
(45) Date of Patent: Nov. 27, 2018

(54) VISUAL VALVE POSITION INDICATOR WITH WIRELESS TRANSMITTER

(71) Applicant: Pentair Flow Services AG, Schaffhausen (CH)

(72) Inventors: Eric Jordan, River Edge, NJ (US); Bill Tatum, Davidson, NC (US)

(73) Assignee: Westlock Controls Corporation, Saddlebrook, NJ (US)

( * ) Notice: Subject to any disclaimer, the term of this patent is extended or adjusted under 35 U.S.C. 154(b) by 0 days.

(21) Appl. No.: 14/598,056

(22) Filed: Jan. 15, 2015

(65) Prior Publication Data

US 2015/0204457 A1 Jul. 23, 2015

Related U.S. Application Data

(60) Provisional application No. 61/928,724, filed on Jan. 17, 2014.

(51) Int. Cl.
*G08B 25/10* (2006.01)
*F16K 37/00* (2006.01)
(Continued)

(52) U.S. Cl.
CPC .......... *G08B 25/10* (2013.01); *A61N 1/0519* (2013.01); *A61N 1/0553* (2013.01); *A61N 1/0556* (2013.01); *A61N 1/36053* (2013.01); *A61N 1/36171* (2013.01); *F16K 37/0033* (2013.01); *F16K 37/0041* (2013.01);
(Continued)

(58) Field of Classification Search
CPC .. G08B 25/10; F16K 37/0033; F16K 37/0041

USPC .......... 340/539.1; 137/485.7, 552, 137, 554, 137/556, 553, 556.3
See application file for complete search history.

(56) References Cited

U.S. PATENT DOCUMENTS

| 4,406,303 A | 9/1983 | Kilmoyer |
| 4,635,901 A | 1/1987 | Pond |

(Continued)

FOREIGN PATENT DOCUMENTS

| WO | 2008078323 A1 | 7/2008 |
| WO | 2013034179 A1 | 3/2013 |

OTHER PUBLICATIONS

Westlock Controls; Wireless Valve Monitoring System; Copyright Westlock ©. All Rights Reserved; pp. 1-26.

*Primary Examiner* — Steven Lim
*Assistant Examiner* — Mancil Littlejohn, Jr.
(74) *Attorney, Agent, or Firm* — Quarles & Brady LLP (57) ABSTRACT

An indicator device with wireless communication functionality for monitoring a position of a valve actuating device. The indicator device including a visual indication device having an outer beacon and an inner beacon received within the outer beacon and arranged to rotate relative to the outer beacon, a wireless module including at least one sensor, positioned within the inner beacon of the visual indication device, and configured to transmit a message using the wireless module, and a shaft extending through the visual indication device and coupled to the valve actuating device. Rotation of the shaft is detectable by the at least one sensor of the wireless module to indicate the position of the valve actuating device, and the indicator device is sealed to inhibit infiltration of liquid and penetration of debris to the wireless module.

20 Claims, 6 Drawing Sheets

(51) Int. Cl.
*A61N 1/05* (2006.01)
*A61N 1/36* (2006.01)

(52) U.S. Cl.
CPC .......... *A61N 1/0558* (2013.01); *A61N 1/3601* (2013.01); *A61N 1/3611* (2013.01); *A61N 1/36135* (2013.01); *A61N 1/36178* (2013.01); *A61N 1/36196* (2013.01)

(56) References Cited

U.S. PATENT DOCUMENTS

| | | | |
|---|---|---|---|
| 4,962,290 A | | 10/1990 | Nelson et al. |
| 5,223,822 A | | 6/1993 | Stommes et al. |
| 5,277,223 A | * | 1/1994 | Glockner ............ F16K 37/0008 137/315.35 |
| 5,623,963 A | | 4/1997 | Stommes et al. |
| 5,647,396 A | | 7/1997 | Stommes et al. |
| 6,021,652 A | | 2/2000 | Walker |
| 6,044,791 A | | 4/2000 | LaMarca et al. |
| 6,079,442 A | | 6/2000 | Raymond, Jr. et al. |
| 6,597,290 B2 | | 7/2003 | Mogi |
| 6,820,647 B1 | * | 11/2004 | Grecco ................. F16K 31/041 137/137 |
| 6,904,476 B2 | | 6/2005 | Hedtke |
| 7,219,691 B2 | | 5/2007 | Gethmann et al. |
| 7,784,490 B1 | | 8/2010 | Stewart et al. |
| 7,819,133 B2 | | 10/2010 | Minervini et al. |
| 7,886,766 B2 | | 2/2011 | Radomsky et al. |
| 7,894,473 B2 | | 2/2011 | Raghavendra et al. |
| 8,096,313 B1 | | 1/2012 | Kah |
| 8,424,563 B2 | | 4/2013 | Haller et al. |
| 8,538,560 B2 | | 9/2013 | Brown et al. |
| 8,555,919 B2 | | 10/2013 | Evatt et al. |
| 2002/0007854 A1 | * | 1/2002 | Dilger .................... G01F 1/363 137/554 |
| 2006/0272710 A1 | * | 12/2006 | Minervini ........... F16K 37/0033 137/487.5 |
| 2007/0034264 A1 | | 2/2007 | Kunz et al. |
| 2008/0078462 A1 | * | 4/2008 | Minervini ........... F16K 37/0058 137/625.64 |
| 2008/0078973 A1 | | 4/2008 | Richards et al. |
| 2009/0027189 A1 | * | 1/2009 | Isaksson ................ G01D 21/00 340/539.1 |
| 2009/0102601 A1 | * | 4/2009 | Mathiesen ......... G05B 19/4185 340/3.1 |
| 2009/0222220 A1 | | 9/2009 | Wilke |
| 2011/0140908 A1 | | 6/2011 | Kosht et al. |
| 2011/0290332 A1 | | 12/2011 | Soldo et al. |
| 2013/0042933 A1 | | 2/2013 | Harper, Jr. |
| 2013/0314239 A1 | * | 11/2013 | Clark ................. F16K 37/0041 340/686.6 |
| 2013/0321166 A1 | | 12/2013 | Gritzo et al. |
| 2013/0327403 A1 | | 12/2013 | Jensen |
| 2014/0151587 A1 | | 6/2014 | La Fountain |

* cited by examiner

VISUAL VALVE POSITION INDICATOR WITH WIRELESS TRANSMITTER

CROSS REFERENCES TO RELATED APPLICATIONS

This application claims the benefit of U.S. Provisional Patent Application No. 61/928,724 filed on Jan. 17, 2014, the entire contents of which are incorporated herein by reference.

BACKGROUND

The subject matter disclosed herein relates generally to monitoring valves or actuators in industrial environments.

Present industrial environments, particularly chemical and petroleum environments, have vast quantities of valves and actuators located over a potentially large area. Due to the potentially volatile nature of these environments, the ability to monitor the status of the valves and actuators throughout the facility is necessary. One way to monitor the status of valves and actuators is to couple position sensors thereto. The position sensors are configured to generate an electrical signal indicative of the position of the valve or actuator. However, this type of monitoring requires hard-wired connections from a controller to each valve and actuator to be monitored, which is both physically and economically limiting in a facility having thousands of valves and actuators to be monitored. Additionally, in facilities such as off shore oil rigs, the additional cost of running all the required wiring is particularly cost prohibitive.

To reduce the cost of hard-wiring sensors, wireless monitoring devices that utilize wireless sensors have been used in the industry. Wireless sensors allow for remote monitoring of valves and actuators, thereby removing the requirement of hard-wiring the position sensors from the valves and actuators to a controller. However, replacement of existing hard-wired position sensors with wireless monitoring devices requires the existing sensor housings to be replaced with new housings that contain the wireless monitoring devices. In existing systems, the ability to update the existing wired monitoring system with a wireless monitoring system could be cost prohibitive due to the labor required to replace the existing housings with new housings.

In addition to electronic monitoring, visual indicators have been used to provide a user with a visual indication of the position of a valve from a distance. This indication can be critical to an operator in the field who may not have access to the position information due to lack of access to the control system. Conventional visual indicators can couple to existing valve position sensor housings and are installed separately from the valve position sensor housings. While these visual indicators can be coupled to multiple housing types, thereby allowing for easy retrofitting to existing modules, these visual indicators only provide visual indication for a user. Thus, the visual indicators are only capable of providing valve or actuator position information to the user within a visual range of the visual indicator.

Thus, there is a need for a visual indication device with an integrated wireless monitoring device to allow for cost effective retrofitting of existing valve or actuator position sensing devices with wireless monitoring capabilities.

SUMMARY

The present embodiments overcome the aforementioned drawbacks by providing a device and method including a visual indicating device with wireless capabilities that can be installed on an existing housing.

In one embodiment the invention provides an indicator device with wireless communication functionality for monitoring a position of a valve actuating device. The indicator device includes a visual indication device having an outer beacon and an inner beacon received within the outer beacon and arranged to rotate relative to the outer beacon, a wireless module including at least one sensor, positioned within the inner beacon of the visual indication device, and configured to transmit a message using the wireless module, and a shaft that extends through the visual indication device and coupled to the valve actuating device. Rotation of the shaft is detectable by the at least one sensor of the wireless module to indicate the position of the valve actuating device, and the indicator device is sealed to inhibit infiltration of liquid and/or penetration of debris to the wireless module.

In another embodiment, the invention provides an indicator device with wireless communication functionality for monitoring a position of a valve actuating device. The indicator device includes an outer beacon sealingly coupled to the valve actuating device to define a sealed interior. A portion of the outer beacon is substantially transparent. An inner beacon is arranged within the sealed interior of the outer beacon and is rotatable relative thereto. The inner beacon defines at least one marking to indicate the position of the valve actuating device. A wireless module is arranged substantially within the inner beacon and within the sealed interior. The wireless module includes at least one sensor and is configured to transmit a message. A shaft extends through the wireless module and engages the inner beacon such that rotation of the shaft induces rotation of the inner beacon and actuation of the wireless module.

In another embodiment, the invention provides a method of retrofitting an indicator device onto a valve actuating device. The method includes inserting an indicator shaft through a central hub of the valve actuating device, coupling the indicator shaft to an output shaft of the valve actuating device such that rotation of the output shaft results in proportional rotation of the indicator shaft, and sealingly engaging the indicator device with mounting features of a valve actuating device housing.

These and other aspects of the disclosure will become apparent in light of the following detailed description.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize that the examples provided herein have many useful alternatives and fall within the scope of embodiments of the invention.

Figure 1:
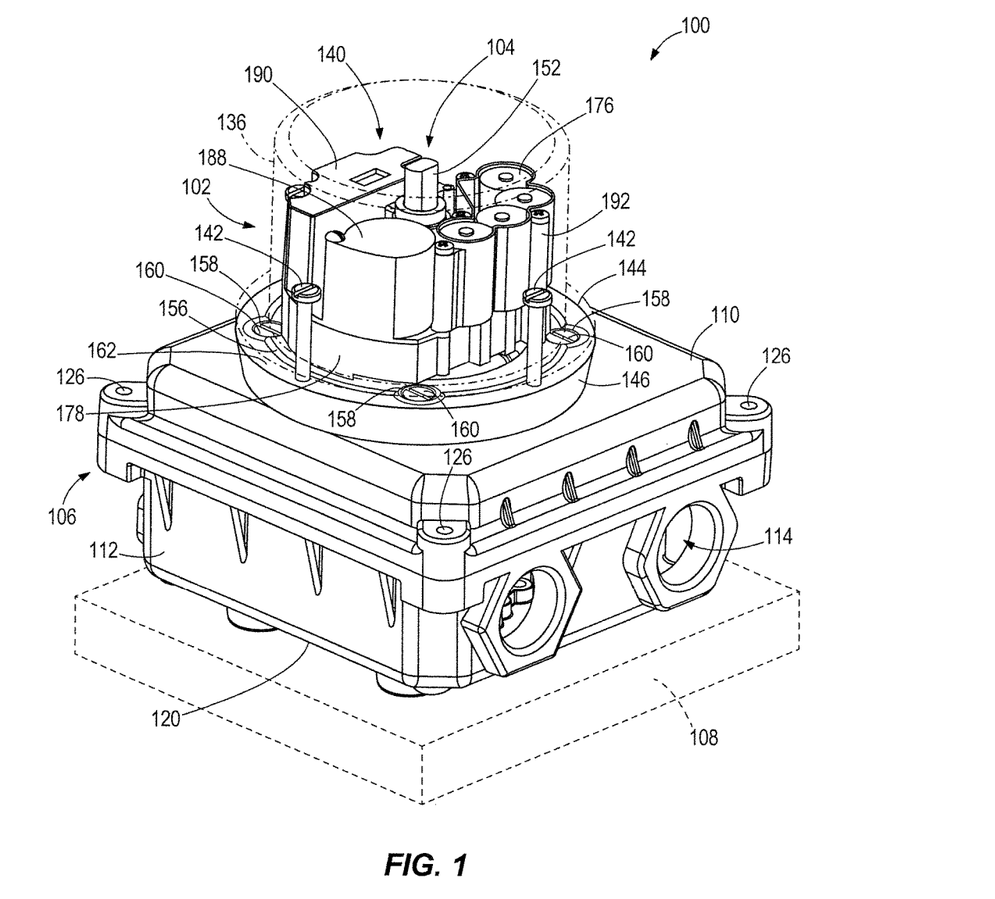
FIG. 1 is a pictorial view of a visual indicator device including a wireless module coupled to a housing.

FIG. 1 illustrates an indicator device 100 including a beacon assembly 102 surrounding a wireless module 104 mounted to a housing 106. In one example, the indicator device 100 may be a visual indicator device. The housing 106 can be positioned between the beacon assembly 102 and an actuation device 108, such as a valve or actuator. The beacon assembly 102 can provide a user with a visual indication of the position of the actuation device 108. In addition, the wireless module 104 can transmit a wireless signal to a receiver indicating a position of the actuation device 108.

The housing 106 includes an upper portion 110 and a lower portion 112. The lower portion 112 defines an opening 114 for access to an interior cavity 116 of the housing 106. The opening 114 can be threaded, or may include a coupling device for coupling a conduit, for example, to the housing 106. Alternatively, the housing 106 may define zero or a plurality of openings as desired for access to the interior cavity 116 of the housing 106.

Figure 2:
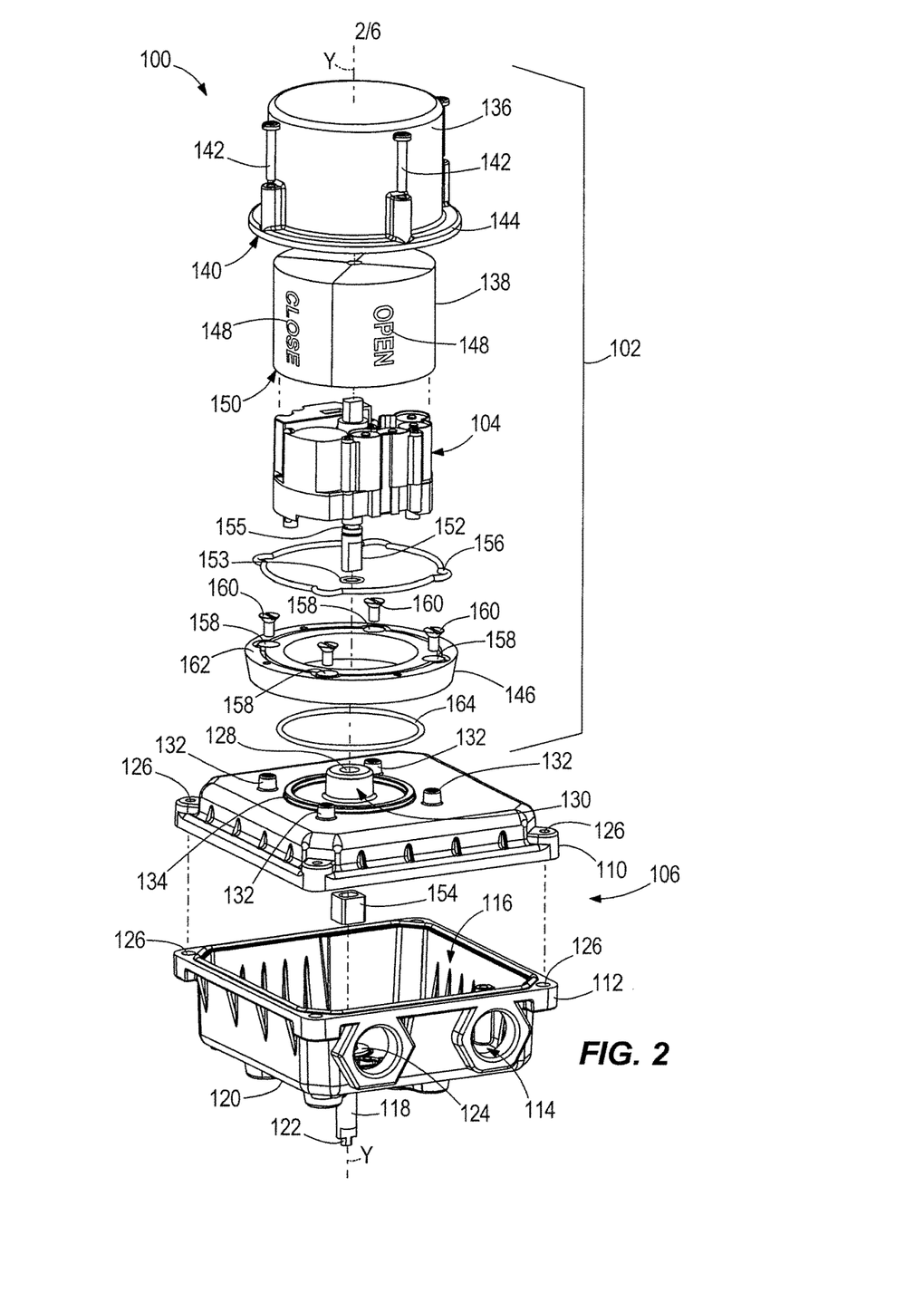
FIG. 2 is an exploded view of the visual indicator device of FIG. 1.

Turning now to FIG. 2, the lower portion 112 of the housing 106 further includes a primary output shaft 118 that may be coupled to the actuation device 108 to indicate a change in position of the actuation device 108. The primary output shaft 118 extends downward from a base 120 of the lower portion 112 of the housing 106 along an axis Y. The primary output shaft 118 may be positioned substantially in the center of the base 120, and rotate along the axis Y within the housing 106. In some embodiments, the primary output shaft 118 may be integrally coupled to the base 120 of the housing 106. Alternatively, the primary output shaft 118 may be joined to the base 120 by any suitable coupling mechanism including, but not limited to, welding, fasteners, adhesive, and the like.

The primary output shaft 118 includes a first end 122 and an opposing second end 124. In one embodiment, the first end 122 can be keyed to interface with a coupling (not shown), such as a valve coupling, when the actuation device 108 is a valve. Alternatively, the first end 122 can be coupled to the actuation device 108 using any suitable coupling device. In one construction, the primary output shaft 118 at the first end 122 can couple to any ISO/DIS 5211.2 F03 manual valve. In another construction, the primary output shaft 118 at the first end 122 may be coupled to an actuator having a NAMUR interface, such as a VDI/VDE 3845 type interface. In other constructions, the primary output shaft 118 at the first end 122 may be coupled to an actuator using a mechanical attachment to the actuation device 108 or actuator shaft as desired.

With continued reference to FIG. 2, the upper portion 110 of the housing 106 is arranged to be selectively fastened to the lower portion 112 of the housing 106 using fasteners (not shown), for example, that extend through corresponding apertures 126 positioned thereon. The upper portion 110 of the housing 106 further defines a secondary shaft opening 128 surrounded by an upwardly extending central hub 130 positioned along the axis Y. The upper portion 110 of the housing 106 further includes mounting features in the form of a plurality of bosses 132, a raised ring 134, and the central hub 130 that are configured to engage elements of the beacon assembly 102, as will be described in further detail below.

While the housing 106 is shown to be of a square design in FIGS. 1 and 2, it is contemplated that the housing 106 may have multiple designs. Non-limiting examples include rectangular designs, cylindrical designs, or any other design required to facilitate installation in the field. Furthermore, it should be known that the housing 106 can be fabricated from a variety of materials. In one example, the housing 106 can be fabricated from metal material. Other non-limiting examples of the housing 106 material include aluminum, steel, brass or any other suitable metal as is known in the art. Alternatively, the housing 106 can be fabricated from a plastic material. In a further embodiment, the upper portion 110 and the lower portion 112 of the housing 106 can be fabricated from different materials, as desired.

The housing 106 can be designed for installation in multiple environments. In one construction, the housing 106 can be an IP66 type housing and designed for resistance to chemicals, ultraviolet rays and/or impact. In a further embodiment, the housing 106 can be explosion proof and designed to be suitable for installation in an FM/IEC/ATEX Zone 0 and/or Class 1 Division 1 environment. In other embodiments, the housing 106 may be designed for other installation environments as are known in the industry, as desired.

With continued reference to FIG. 2, an exploded view of the beacon assembly 102 is shown. The illustrated beacon assembly 102 includes an outer beacon 136 that encloses an inner beacon 138. The outer beacon 136 may be substantially cylindrical in shape and define a hollow, interior cavity 140 for receiving the inner beacon 138. The outer beacon 136 may be configured to receive assembly screws 142 on a circumferential edge 144 to couple the beacon assembly 102 to an adaptor ring 146, as will be described in further detail below.

In one construction, the outer beacon 136 can be constructed from a transparent material, as shown in FIG. 1, to allow the inner beacon 138 to be visible to a user. Alternatively, the outer beacon 136 can be constructed from an opaque material, or the outer beacon 136 can be constructed from a combination of transparent materials and opaque materials. In addition, the outer beacon 136 can be constructed from any suitable material including, but not limited to, a plastic material, a UV resistant co-polyester, a chemical resistant material, stainless steel, a material suitable for use in an explosion proof environment, and the like.

The beacon assembly 102 may include various types of visual indicators. Thus, the inner beacon 138 can be made of a plastic material and include markings 148 indicating the position of the actuation device 108. In one non-limiting example, the markings 148 may be characterized by a color for indicating the position of the actuation device 108. As shown in the embodiment of FIG. 2, the markings 148 may include printed words (e.g., "open" and "close") indicating the position of the actuation device 108. The inner beacon 138 may also be characterized by multiple colors. For example, the inner beacon 138 can be a black color, an ANSI Blue color for use in gas-low hazard environments, an ANSI Red color for use in fire quenching environments, or another color, as desired.

Similar to the outer beacon 136, the inner beacon 138 may be substantially cylindrical in shape and dimensioned to be positioned inside the interior cavity 140 of the outer beacon 136. The inner beacon 138 may also include a hollow cavity 150 that is dimensioned to receive the wireless module 104. The wireless module 104 includes an output shaft 152 that may be coupled to the second end 124 of the primary output shaft 118 via a shaft coupler 154 positioned in the interior cavity 116 of the housing 106. The output shaft 152 extends through the upper portion 110 of the housing 106 at the secondary shaft opening 128 defined by the central hub 130 and couples to the primary output shaft 118 with the shaft coupler 154. Alternatively, the output shaft 118 or 152 may extend through the entire assembly. It should be known that the shaft coupler 154 can be any coupler as is known in the art. At an opposing end, the output shaft 152 is coupled to the inner beacon 138. Thus, the inner beacon 138 can rotate when the primary output shaft 118 is rotated, thereby providing visual indication to a user of the position of the actuation device 108.

The output shaft 152 includes a sealing feature in the form of an o-ring 153 received in an o-ring groove 155 positioned and arranged to sealingly engage the interior of the central hub 130. The sealing feature inhibits infiltration of liquid and/or penetration of debris into the beacon assembly 102.

Once the wireless module 104 is installed into the inner beacon 138, the wireless module 104 and inner beacon 138 are coupled to the outer beacon 136 at the adaptor ring 146. An outer beacon gasket 156 is installed between the outer beacon 136 and the adaptor ring 146. The outer beacon 136 may be coupled to the adaptor ring 146 with the assembly screws 142 that are configured to be received by corresponding apertures 158 extending through the adaptor ring. 146.

Similarly, the beacon assembly 102 may be coupled to the upper portion 110 of the housing 106 via assembly screws 160 that extend through a perimeter portion 162 of the adaptor ring 146. The assembly screws 160 are configured to engage the bosses 132 of the upper portion 110 of the housing 106 to secure the beacon assembly 102 to the housing 106. A sealing gasket 164 that circumscribes the raised ring 134 disposed on the upper portion 110 of the housing 106 may be provided between the adaptor ring 146 and the upper portion 110 of the housing 106. The sealing gasket 164 can be an o-ring, for example, or any other suitable sealing gasket.

The adaptor ring 146 is a single example chosen from a plurality of adapter rings. Various adapter rings can be made for use with a wide variety of housings 106 such that the beacon assembly 102 can be mounted onto all sorts of different housings, as are used across various industries. For example, the hole pattern and other mounting features may be different on separate adapter rings to correspond with the desired housing.

Figure 3:
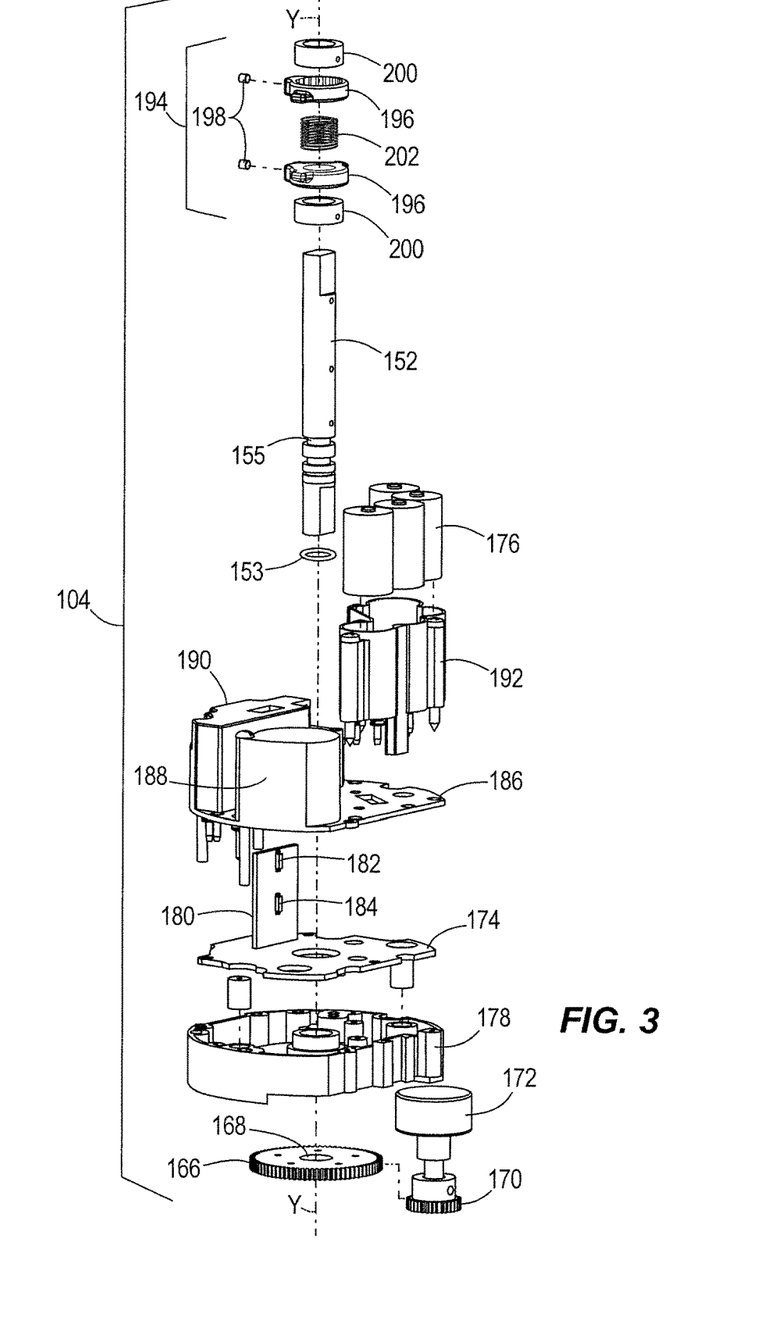
FIG. 3 is an exploded view of the wireless module of FIG. 1.
Figure 4:
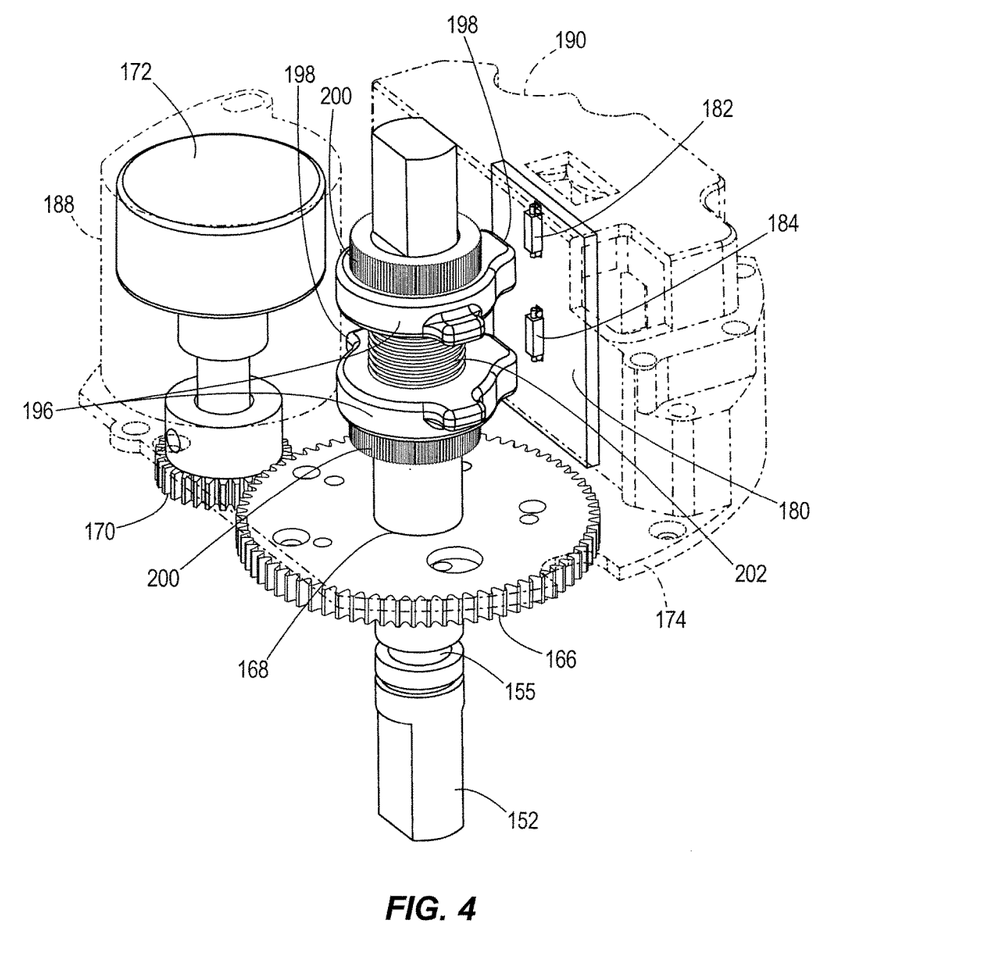
FIG. 4 is a detailed pictorial view of a position sensor of the wireless module of FIG. 1.

Turning now to FIGS. 3 and 4, detailed views of the wireless module 104 are shown. More particularly, the wireless module 104 includes a primary output gear 166 with a centrally disposed aperture 168 configured to receive and engage the primary output shaft 118 of the housing 106. The primary output gear 166 drives a position gear 170 which is coupled to a potentiometer 172. The potentiometer 172 may be supplied with a voltage from a main electronics board 174. In another embodiment, the potentiometer 172 can be supplied a voltage directly from a battery pack 176. The potentiometer 172 provides an output voltage to the electronics board 174 based on a position of the position gear 170 that corresponds to a position of the output shaft 152, which, as previously described, engages the primary output shaft 118. In one example, the potentiometer 172 may be capable of recognizing rotation of the output shaft 152 with a resolution of about 0.1 degrees. Thus, the accuracy of the potentiometer 172 allows the visual indicating device to accurately display the position of the actuation device 108 at any point between the open position and the closed position. The potentiometer 172 is coupled to an electronics canister 178, that provides a mounting location for the main electronics board 174. The main electronics board 174 contains decoding circuitry, wireless transmission circuitry, and a sensor board 180 including a first hall sensor 182 and a second hall sensor 184, for example. In another embodiment, the sensor board 180 can have one, three, or more hall sensors.

The wireless module 104 further includes an electronics cover 186. The electronics cover 186 couples to the main electronics board 174 and includes a potentiometer housing 188 for housing the potentiometer 172, and a sensor housing 190 for mounting the sensor board 180 thereto (see FIG. 4). The electronics cover 186 may also be coupled to a battery canister 192 that houses the battery pack 176 used to power the wireless module 104. In one embodiment, the battery pack 176 can contain lithium type batteries. Alternatively, the battery pack 176 can contain alkali type batteries or any other suitable battery types that are known in the industry.

Figure 5:
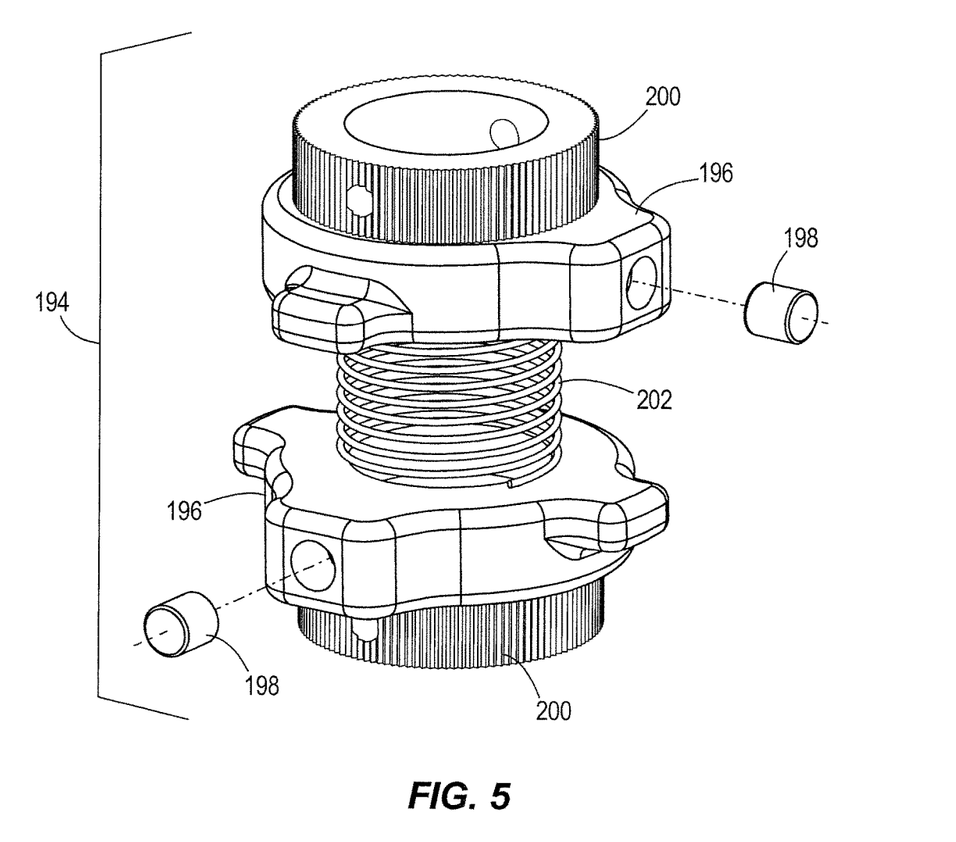
FIG. 5 is a detailed pictorial view of an embodiment of a cam assembly of the wireless module of FIG. 4.

The wireless module 104 also includes a cam assembly 194, as best shown in FIG. 5. The cam assembly 194 is configured to engage the output shaft 152 of the wireless module 104 (see FIG. 4). The cam assembly 194 may further include a pair of cam triggers 196, a plurality of magnet triggers 198, a pair of splines 200, and a compression spring 202 for interfacing with the sensor board 180. In an alternate embodiment, the cam assembly 194 can have a single cam trigger 196. In FIG. 4, the interface of the pair of cam triggers 196 and the plurality of magnet triggers 198 to the sensor board 180 is shown. In one embodiment, one of the plurality of magnet triggers 198 can be pressed into and fixed within each of the cam triggers 196. The pair of cam triggers 196 define an internal spline which meshes with the pair of splines 200. The pair of cam triggers 196 and the pair of splines 200 may be positioned on opposing ends of the compression spring 202.

Returning now to FIG. 4, the cam assembly 194 can be positioned on the output shaft 152. The pair of splines 200 may be coupled to the output shaft 152 using a locking device in the form of a press fit roll pin, for example. Alternatively, the locking device can be a set screw, or any locking device as desired. The plurality of magnet triggers 198 embedded in the pair of cam triggers 196 can be offset by about 90 degrees, as shown in FIG. 5. Alternatively, the plurality of magnet triggers 198 embedded in the pair of cam triggers 196 can be offset by 180 degrees, or a user can offset the plurality of magnet triggers 198 embedded in the pair of cam triggers 196 by moving the pair cam triggers 196 into a desired position prior to mating the pair of cam triggers 196 to the pair of splines 200.

The plurality of magnet triggers 198 may be arranged to pass at least one of the first hall sensor 182 and the second hall sensor 184 as the output shaft 152 is rotated. For example, one of the plurality of magnet triggers 198 that passes the first hall sensor 182 may generate an electrical signal indicating that the actuation device 108 is in a closed position. A different electrical signal may be generated by another one of the plurality of magnet triggers 198 that passes by the first hall sensor 182 to indicate that the actuation device 108 is in an open position, for example. Additionally, or alternatively, the magnet trigger 198 passing by the second hall sensor 184 may generate an electrical signal indicating that the actuation device 108 is in a closed position. Similarly, a different electrical signal may be generated by the magnet trigger 198 passing by the second hall sensor 184 indicating that the actuation device 108 is in an open position.

During operation, the wireless module 104 can be configured to transmit a message to a user interface, for example, accessible by a user. The message transmitted by the wireless module 104 can be a position of the actuation device 108 (e.g., opened or closed). Additionally, or alternatively, the wireless module 104 can monitor and transmit additional status information of the actuation device 108 including a temperature status and/or diagnostic information of the actuation device 108. In one example, the wireless module 104 can transmit diagnostic information, such as a battery status or alarm associated with the wireless module 104. Messages transmitted by the wireless module 104 can be transmitted with a time stamp to inform the user, for example, when a particular message and/or alert occurred. In some embodiments, the wireless module 104 can transmit a message at pre-determined time intervals to ensure the user is continuously aware of the position of the actuation device 108, or any diagnostic information related to the actuation device 108 and/or the wireless module 104. For example, the pre-determined time interval can be 15 minutes, or any other suitable time interval determined by a user. The wireless module 104 may include and transmit any combination of the above and other features, as desired.

In addition, the wireless module 104 can be placed on the valve actuation device 108 that may be suspicious or is needing excess maintenance to troubleshoot the performance of the valve. The installation of the wireless module 104 does not affect the existing installation of the valve actuation device 108 and thus, the wireless module 104 can be used temporarily and removed and reinstalled on another valve actuation device 108. Used as a diagnostic tool, the beacon assembly 102 is capable of collecting and analyzing data received from the valve actuation device 108 to diagnose issues with the valve. For example, the diagnostic tool may be capable of sending messages for a potential maintenance situation and its severity, as well as messages to schedule component replacement before failure and end of life occurs. Additionally, the diagnostic tool may generate messages relating to one or more of the operating parameters of the valve actuation device 108.

In one embodiment, the wireless module 104 can communicate using a standard wireless protocol. The standard wireless protocol can be based on Zigbee Pro that may contain built-in AES 128-bit encryption security, for example. In alternative embodiments, the wireless protocol can be based on the WirelessHART protocol or an ISA SP100 protocol.

Figure 6:
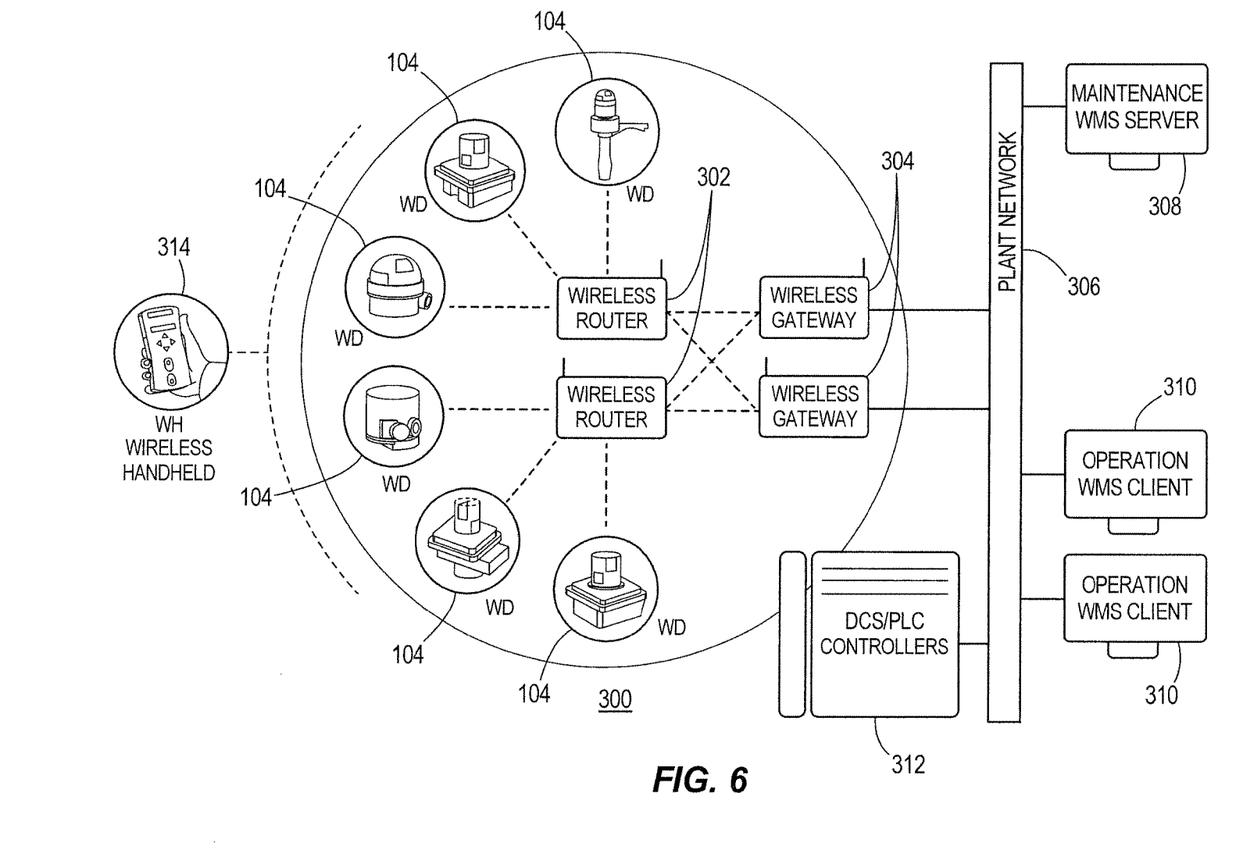
FIG. 6 is a schematic view of a wireless system architecture including the visual indicator device of FIG. 1.

Turning now to FIG. 6, a representative system architecture 300 is shown. The representative system architecture 300 is an example of a typical system environment in which one or more indicator devices 100 may operate. The representative system architecture 300 can include a plurality of the wireless modules 104. The wireless modules 104 can communicate a message via a wireless protocol to one or more wireless routers 302. The wireless routers 302 can transmit the message from any one of the wireless modules 104 to one or more wireless gateways 304. The wireless gateways 304 can be connected via a wired connection to a plant network 306. Once the message from the wireless module 104 is available on the plant network 306, the message can be accessed by a network device with access to the plant network 306.

In one embodiment, the network device can be a maintenance server 308. In another embodiment, the network device can be an operation client terminal 310. In yet a further embodiment, the network device can be a plant control system 312. The plant control system 312 can be a distributed control system (DCS), a supervisory control and data acquisition (SCADA) system, or a programmable logic controller (PLC) type system. The plant control system 312, in an alternative embodiment, could also be any type of plant control system as is known in the art. In some embodiments, the wireless module 104 can transmit a message to a handheld network device 314 (e.g., laptop, smartphone, tablet, and the like) that is remotely accessible by a user. The wireless modules 104 can be configured using a mesh network topology that can ensure full redundancy. A mesh network topology can also inhibit a network failure where a single point of failure exists. Alternatively, the network topology can be a star type topology or a ring type topology, for example.

An advantage of the beacon assembly 102 is the sealing arrangement with the housing 106. The structural arrangement of the beacon assembly 102 including the outer beacon gasket 156, the sealing gasket 164 and the sealing arrangement of the output shaft 152 inhibit liquid infiltration and/or debris penetration of the beacon assembly 102.

Another advantage of the beacon assembly 102 is the ability to retrofit to any existing valve assembly without replacing the existing device or disturbing existing wiring or operations of the valve. In a retrofitting operation, the indicator shaft 152 of the wireless module 104 may be inserted through the central hub 130 of any valve actuating device 108. Upon insertion through the central hub 130, the indicator shaft 152 engages the output shaft 102 and is coupled thereto. Rotation of the output shaft 102 results in proportional rotation of the indicator shaft 152. Thus, the retrofitting capabilities of the beacon assembly 102 to any valve actuation device 108 allows for maximum re-use of existing equipment and is therefore more economical than a complete new installation. In addition, service interruptions can be minimized and upgrading the beacon assembly 102 is quick and easy.

Yet another advantage provided by the invention is the use of the beacon assembly 102 as a diagnostic tool. The diagnostic tool is capable of transmitting a message indicative of the position of the actuation device 108, as well as other status or diagnostic information of the valve actuation device 108. The diagnostic tool of the wireless module 104 can be placed on a valve actuation device that is suspicious or is needing maintenance to troubleshoot the performance of the valve. The installation of the wireless module 104 does not affect the existing installation of the valve actuation device and thus, the wireless module 104 can be used temporarily and removed and reinstalled on another valve actuation device when the wireless module 104 is finished collecting the necessary data to diagnose issues with the valve.

Another advantage of the beacon assembly 102 is the arrangement of the wireless module 104 fully within the inner beacon 138. This arrangement provides a compact beacon assembly 102 that provides both visual and wireless indication.

It will be appreciated by those skilled in the art that while the invention has been described above in connection with particular embodiments and examples, the invention is not necessarily so limited, and that numerous other embodiments, examples, uses, modifications and departures from the embodiments, are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

We claim:

1. An indicator device with wireless communication functionality for monitoring a position of a valve actuating device, the indicator device comprising:
   a visual indication device including an outer beacon and an inner beacon received within the outer beacon and arranged to rotate relative to the outer beacon;
   an adapter ring coupled to the outer beacon, the adapter ring having a channel through a center thereof;
   a first seal positioned between and contacted by the outer beacon and the adapter ring;
   a central hub extending upwardly from the valve actuating device and having a shaft opening formed through a center thereof;
   a wireless module including at least one sensor, the wireless module positioned within the inner beacon of the visual indication device and configured to transmit a message using the wireless module; and
   a shaft extending through the visual indication device and through the central hub of the valve actuating device, wherein rotation of the shaft is detectable by the at least one sensor of the wireless module to indicate the position of the valve actuating device,
   wherein the indicator device is configured to be removably coupled to an outer surface of the valve actuating device with a second seal positioned between the adapter ring and the valve actuating device to inhibit at least one of infiltration of liquid and penetration of debris to the wireless module and the inner beacon is configured to rotate relative to the adapter ring.

2. The indicator device of claim 1, wherein the indicator device is sealed with respect to the valve actuating device.

3. The indicator device of claim 1, wherein the wireless module utilizes a wireless communication protocol, the wireless communication protocol including at least one of a Zigbee Pro protocol, a WirelessHART protocol, and an ISA SP100 protocol.

4. The indicator device of claim 1, wherein the message transmitted by the wireless module includes a position message indicating the position of the actuating device.

5. The indicator device of claim 1, wherein the message transmitted by the wireless module includes a diagnostic message corresponding to at least one of the actuating device, the wireless module, and the visual indicating device.

6. The indicator device of claim 1, wherein the wireless module is configured to transmit the message at a predetermined time interval.

7. The indicator device of claim 1, wherein the shaft is sealingly coupled to the valve actuating device.

8. The indicator device of claim 1, wherein the visual indication device includes at least one marking to indicate the position of the valve actuating device.

9. The indicator device of claim 8, wherein the visual indication device is constructed from a transparent material enabling the at least one marking to be visible therethrough.

10. The indicator device of claim 1, wherein the wireless module is positioned entirely within the inner beacon.

11. The indicator device of claim 1, wherein the wireless module is powered by a battery.

12. The indicator device of claim 1, wherein the channel through the center of the adapter ring is configured to receive a portion of the first seal.

13. The indicator device of claim 1, wherein the inner beacon is positioned radially inward from the channel formed in the adaptor ring.

14. An indicator device with wireless communication functionality for monitoring a position of a valve actuating device, the indicator device comprising:
   an outer beacon defining a sealed interior, wherein a portion of the outer beacon is substantially transparent;
   an inner beacon arranged within the sealed interior of the outer beacon and rotatable relative thereto, the inner beacon defining at least one marking to indicate the position of the valve actuating device;
   an adapter ring coupled to the outer beacon;
   a first seal positioned between and contacted by the outer beacon and the adapter ring;
   a wireless module arranged substantially within the inner beacon and within the sealed interior, the wireless module including at least one sensor and configured to transmit a message;
   a shaft extending through the wireless module and engaging the inner beacon such that rotation of the shaft induces rotation of the inner beacon and actuation of the wireless module;
   wherein the adapter ring is configured to be removably coupled to an outer surface of the valve actuating device with a second seal positioned between the adapter ring and the valve actuating device and the inner beacon is configured to rotate relative to the adapter ring.

15. The indicator device of claim 14, wherein the wireless module is powered by at least one battery.

16. The indicator device of claim 14, wherein the indicator device is substantially sealed to inhibit at least one of infiltration of liquid and penetration of debris into the indicator device.

17. The indicator device of claim 14, wherein the adapter ring is selected from one of a plurality of adapter rings and includes mounting features that correspond to the valve actuating device.

18. A method of retrofitting an indicator device onto a valve actuating device, the valve actuating device including a housing defining mounting features and a central hub, and an output shaft,
   the indicator device including:

a visual indication device including an outer beacon and an inner beacon received within the outer beacon and arranged to rotate relative to the outer beacon, an adapter ring coupled to the outer beacon;

a first seal positioned between and contacted by the outer beacon and the adapter ring;

the central hub extending upwardly from the valve actuating device and having a shaft opening formed through a center thereof;

a wireless module including at least one sensor, the wireless module positioned within the inner beacon of the visual indication device and configured to transmit a message using the wireless module, and an indicator shaft extending through the visual indication device and coupled to the output shaft of the valve actuating device, wherein rotation of the indicator shaft is detectable by the at least one sensor of the wireless module to indicate the position of the valve actuating device, wherein the indicator device is configured to be removably coupled to an outer surface of the valve actuating device with a second seal positioned between the adapter ring and the valve actuating device to inhibit at least one of infiltration of liquid and penetration of debris to the wireless module and the inner beacon is configured to rotate relative to the adapter ring, the method comprising:

inserting the indicator shaft through the central hub of the valve actuating device;

coupling the indicator shaft to the output shaft such that rotation of the output shaft results in proportional rotation of the indicator shaft; and sealingly engaging the indicator device with the first and second seals.

19. The method of claim 18, further comprising selecting the adapter ring that corresponds with the mounting features of the housing from a plurality of different adapter rings.

20. The method of claim 18, wherein a first adapter ring is selected for a first valve actuating device and a second adapter ring is selected for a second valve actuating device.

* * * * *